United States Patent [19]
Hyldig-Nielsen et al.

[11] Patent Number: 5,985,563
[45] Date of Patent: Nov. 16, 1999

[54] DETECTION OF RIBOSOMAL RNA USING PNA PROBES

[75] Inventors: Jens Jørgen Hyldig-Nielsen, Vanløse; Michael Anders Godskesen, Vedbæk, both of Denmark

[73] Assignee: Dako A/S, Glostrup, Denmark

[21] Appl. No.: 08/869,454

[22] Filed: Jun. 5, 1997

Related U.S. Application Data

[62] Division of application No. 08/443,930, May 18, 1995.

[30] Foreign Application Priority Data

May 19, 1994 [DK] Denmark ................................. 0572/94

[51] Int. Cl.[6] .............................. C12Q 1/68; C07H 19/00; C07H 21/02; C07H 21/04
[52] U.S. Cl. ............................... 435/6; 514/44; 536/22.1; 536/23.1; 536/24.31; 536/25.32
[58] Field of Search ................... 435/6; 514/44; 536/22.1, 23.1, 24.31, 25.32

[56] References Cited

U.S. PATENT DOCUMENTS

| | | | |
|---|---|---|---|
| 5,173,401 | 12/1992 | Wolffe et al. | 435/6 |
| 5,217,866 | 6/1993 | Summerton et al. | 435/6 |
| 5,316,784 | 5/1994 | Maurer et al. | 427/2 |
| 5,378,606 | 1/1995 | Stern et al. | 435/6 |
| 5,538,896 | 7/1996 | Siciliano et al. | 435/91.2 |
| 5,612,458 | 3/1997 | Hyldig-Nielsen et al. | 530/388.21 |
| 5,629,147 | 5/1997 | Asgari et al. | 435/5 |

FOREIGN PATENT DOCUMENTS

| | | | |
|---|---|---|---|
| 272009 | of 1988 | European Pat. Off. | C12Q 1/68 |
| 408077 | of 1991 | European Pat. Off. | C12Q 1/68 |
| 408078 | of 1991 | European Pat. Off. | G01N 33/547 |
| 131052 | of 1993 | European Pat. Off. | C12Q 1/68 |
| WO 90/10715 | 9/1990 | WIPO | C12Q 1/68 |
| 9015159 | 12/1990 | WIPO | C07K 5/00 |
| 9220702 | 11/1992 | WIPO | C12K 1/68 |
| 9220703 | 11/1992 | WIPO | C12Q 1/68 |
| WO 92/22467 | 12/1992 | WIPO | C12N 15/00 |
| 9301498 | of 1993 | WIPO | G01N 33/543 |
| WO 93/24652 | of 1993 | WIPO | C12Q 1/68 |
| WO 93/24652 | 12/1993 | WIPO | C12Q 1/68 |
| WO 94/02642 | 2/1994 | WIPO | C12Q 1/68 |
| WO 94/02645 | 2/1994 | WIPO | C12Q 1/68 |
| 9517430 | of 1995 | WIPO | C07K 16/44 |
| WO 95/08556 | 3/1995 | WIPO | C07H 21/00 |
| WO 96/36734 | 11/1996 | WIPO | C12Q 1/68 |
| WO 97/14026 | 4/1997 | WIPO | . |

OTHER PUBLICATIONS

Egholm et al; Nature, 365; 566–568 (1993).
Nielsen et al, BioConj. Chem., 5; 3–7 (1994).
Egholm et al, J.A.C.S. 114; 1895–1897 (1992).
Young et al, Nucleic Acid Hybridization, JDL Press (1985) pp.62–65.
Johannsson et al; ELISA and Other Solid Phase Immunoassays, John Wiley & Sons (1988) pp. 85–106.
Buchardt et al, TIBTECH, vol. 11, Sep. 1993, 584–586, 11:384–386.
Faseb Journal, Am. Soc. Biochem. Mol. Biol., Abstracts, Apr. 19, 1994.
Poster Presentation at 85th Annual Meeting Am. Soc. Biochem. Mol. Bio., May 21–25, 1994.
Nielsen et al, Science, vol. 254, 1497–1500 (1991).
Hyrup et al, J. Am. Chem. Soc., vol. 116, 7964–7970 (1994).
Hanvey et al, Science, vol. 258, 1481–11485 (1992).
Rose, ANAL. CHEM., vol. 65 3545–3549 (1993).

*Primary Examiner*—Ardin H. Marschel
*Assistant Examiner*—Jezia Riley
*Attorney, Agent, or Firm*—Graham & James LLP

[57] ABSTRACT

PNA probes for detection of Neisseria gonorrhoeae and Chlamydia trachomatis.

Specific peptide nucleic acid (PNA) probes for detecting a sexual transmitted disease caused by Neisseria gonorrhoeae or Chlamydia trachomatis comprising N-(2-aminoethyl)glycine units in amide linkage with the glycine nitrogen connected to naturally occurring nucleobases or non-naturally occurring nucleobases by a methylene carbonyl linker and said probes capable of hybridizing to 16S or 23S rRNA or rDNA of Neisseria gonorrhoeae or Chlamydia trachomatis are described.

PNA is a very stable molecule with very high affinity for nucleic acid allowing a PNA probe to be shorter than conventional nucleic acid probes.

38 Claims, No Drawings

DETECTION OF RIBOSOMAL RNA USING PNA PROBES

CROSS-REFERENCE

This is a division of Ser. No. 08/443,930 filed on May 18, 1995.

The present invention relates to specific peptide nucleic acid (PNA) probes and methods for detecting a sexual transmitted disease caused by Neisseria gonorrhoeae or Chlamydia trachomatis. More particularly, the invention relates to peptide nucleic acid (PNA) probes capable of hybridizing to 16S or 23S rRNA or DNA from the area coding for said rRNA of Neisseria gonorrhoeae or Chlamydia trachomatis in test samples which may contain Neisseria gonorrhoeae and/or Chlamydia trachomatis.

N. gonorrhoeae, the pathogen of gonorrhoea, is still today a very frequent infectious disease worldwide. In males, the genital infection manifests itself as a purulent inflammation and swelling of the urethra. These symptoms occur in 90% of cases of infection. If left untreated, the infection can ascend and after several weeks produce symptoms of prostatitis. In women, no or only slight symptoms occur in 50% of cases of infection. The infection primarily affects the cervix, but also the urethra. In 10 to 15% of women, the infection spreads to the fallopian tubes and can also lead, inter alia, to sterility. Since the course of the infections is often asymptomatic, many carriers contribute unknowingly to the spread of the disease.

Another very wide spread sexual transmitted disease is caused by Chlamydia trachomatis. Among the more serious complications of C. trachomatis infections are ecotropic pregnancy and tubal infertility.

Considering the impact that these two organisms have, rapid and specific diagnostic tests are of utmost importance.

Diagnosis based on selective growth of the pathogenic bacteria is still the "golden standard", but cell culturing is time-consuming and many clinical isolates are difficult to grow in vitro.

Some of the attempts to replace the slow methods based on cell culturing with faster methods have been based on nucleic acid hybridization using target specific probes.

Attempts have also been made to use nucleic acid probes for diagnosis of infections caused by Neisseria gonorrhoeae or Chlamydia trachomatis.

Nucleic acid probes have to fulfil two criteria in order to be used diagnostically. They must be specific, i.e. the probe should only hybridize to the nucleic acid of the pathogen to be detected in order to exclude false positive test results. They must also be sensitive, i.e. the detection of only a few target molecules should also be possible in order to exclude false negative test results during the early or persistive stages of the infection. It is possible to specifically detect organisms using nucleic acid probes which are complementary to ribosomal RNA (rRNA). Methods based on probes directed against rRNA are very sensitive as many target molecules ($10^3$–$10^4$ copies) are present in each cell.

Methods for identification of organisms using rRNA specific nucleic acid probes have been described in different publications, see e.g. EP-B 0 131 052.

Nucleic acid probes for detection of rRNA of Neisseria gonorrhoeae have been described in EP-A 0 272 009, EP-A 0 408 077 and EP-A 0 574 852. Nucleic acid probes for detection rRNA of Chlamydia trachomatis have been described in WO 90/15159.

Prokaryotic organisms have rRNA molecules which include 5S, 16S and 23S rRNA. Particularly probes complementary to the 16S and/or 23S rRNAs have been used for hybridization as it is known that species variable regions exist within these highly conserved sequences which can be used for species specific probes. However, as rRNAs are generally highly conserved between related species, it will often be difficult to define nucleic acid probes sufficiently specific in terms of species to be able to obtain the required specificity and sensitivity. Another consequence of the conserved character of the rRNA is that the differentiation between two organisms is often based on only one or a few mismatches only in the target sequence which puts high constraints on the stringency needed in the hybridization reaction. A slight deviation from these conditions may result in misidentification.

A very high degree of sequence homology between rRNA of different Neisseria strains makes it difficult to define species specific probes. To obtain the necessary specificity, it is an advantage to use probes as small as possible where the sequence difference between the species makes up a significant proportion of the probe. Typically used nucleic acid probes comprising less than 20 nucleotides are often unable to give reliable results as the melting temperature, $T_m$, for typically used nucleic acid complexes is too low.

The melting temperature, $T_m$, refers to the temperature at which the strands of a nucleic acid hybrid are half dissociated or denatured.

One of the objects of the present invention was, therefore, to provide relative short species specific probes for detecting Neisseria gonorrhoeae or Chlamydia trachomatis without simultaneously compromising the robustness and sensitivity of the assay.

This object is achieved by selecting a peptide nucleic acid (PNA) probe comprising N-(2-aminoethyl)glycine units in amide linkage with the glycine nitrogen connected to purine or pyrimidine bases by a methylene carbonyl linker and capable of hybridizing to 16S or 23S rRNA or DNA from the area coding for said rRNA of Neisseria gonorrhoeae or Chlamydia trachomatis.

The present PNA probes form complexes with complementary nucleic acids which complexes are considerably more stable (higher $T_m$ value) than would be a similar hybrid formed by a typically used nucleic acid probe of corresponding sequence allowing sensitive assays to be made with shorter probes than is the case of typical nucleic acid probes used today.

Hybridization with traditionally used nucleic acid probes is much faster in solution than in solid phase hybridization. Due to the high affinity of PNA for nucleic acid, even solid phase hybridization between PNA probes and nucleic acid can be performed rapidly allowing greater flexibility in the assay format. Hybridization efficiency is only slightly influenced by pH and salt concentration in the hybridization solution allowing PNAs to hybridize under conditions not favourable for ordinary DNA probes.

Furthermore, PNAs have a higher thermal instability of mismatching bases whereby PNAs exhibit a greater specificity for their complementary nucleic acids than traditionally used nucleic acid probes of corresponding sequence would do (WO 92120703).

The structure of PNA is not degraded by nucleases or proteases making the PNA molecule very stable in biological solutions.

The present invention relates to PNA probes for detecting Neisseria gonorrhoeae or Chlamydia trachomatis comprising from 6 to 30 N-(2-aminoethyl)glycine units, particularly from 8 to 20 N-(2-aminoethyl)glycine units, in amide linkage with the glycine nitrogen connected to naturally occurring nucleobases or non-naturally occurring nucleobases by a methylene carbonyl linker or connected to a labelling group and said probe capable of hybridizing to 16S or 23S rRNA or DNA from the area coding for said rRNA of Neisseria gonorrhoeae or Chlamydia trachomatis.

In addition to the backbone and bases, the PNA probes according to the invention may optionally have pendant groups, usually at the termini, to stabilize the end, to label the probe or to increase the solubility.

Furthermore, the invention relates to a method for the detection of sexual transmitted diseases caused by Neisseria gonorrhoeae or Chlamydia trachomatis using at least one PNA probe under hybridization conditions followed by detection of the hybrid formation, which method is characterized in that one or more of the PNA probes according to the present invention is used for specific detection.

A further object of the present invention is test kits for use in the detection of diseases caused by Neisseria gonorrhoeae and/or Chlamydia trachomatis, comprising at least one PNA probe according to the invention and at least one detection reagent.

Peptide nucleic acids (PNAs) are described in WO 92/20702 as compounds comprising a polyamide backbone bearing a plurality of ligands such as naturally occurring nucleobases attached to a polyamide backbone through a suitable linker. It has recently been shown that PNA, in which the backbone is structurally homomorphous with the ribose phosphate backbone and consists of N-(2-aminoethyl)glycine units to which nucleobases are attached, is able to hybridize to complementary oligonucleotides to form PNA-nucleic acid complexes (Egholm et al., Nature, vol 365, 566–568 (1993)).

The use of peptide nucleic acids in a method for detecting, identifying or quantitating a target nucleic acid is described in WO 92/20703. However, there is no specific exemplification of useful probes and assay methods.

The present invention relates to a group of peptide nucleic acids of particular relevance in detection of sexual transmitted diseases caused by Neisseria gonorrhoeae or Chlamydia trachomatis. The present PNA probes comprise from 6 to 30 N-(2-aminoethyl)glycine units in amide linkage with the glycine nitrogen connected to naturally occurring nucleobases or non-naturally occurring nucleobases by a methylene carbonyl linker or connected to a labelling group and said probes being capable of hybridizing to 16S or 23S rRNA or DNA from the area coding for said rRNA of Neisseria gonorrhoeae or Chlamydia trachomatis.

Traditionally, hybridization is understood as the process by which, under predetermined reaction conditions, two partially or completely complementary strands of nucleic acid are allowed to come together in antiparallel fashion to form a double-stranded nucleic acid with specific and stable hydrogen bonds.

The backbone of the PNA probes according to the present invention is structurally homomorphous with the ribose phosphate backbone of traditionally used nucleic acids allowing hybridization to occur.

PNAs with the present backbone can form duplexes in either orientation, but the antiparallel orientation forms the most regular and stable duplex. Hence the antiparallel configuration is preferred for probe applications. Duplex in antiparallel orientation can be illustrated as follows

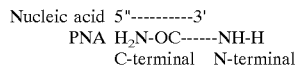

Nucleic acid 5"----------3'
PNA H₂N-OC------NH-H
C-terminal   N-terminal

Mainly because the PNA strand is uncharged, a PNA-nucleic acid-duplex will have a higher $T_m$ than the corresponding nucleic acid-nucleic acid-duplex. Typically there will be an increase in $T_m$ of about 1° C. per basepair at 100 mM NaCl depending on the sequence (Egholm et al. (1993), Nature, 365, 566–568).

Due to this higher affinity, significantly shorter PNA oligomers can be applied in probe based analysis as opposed to the 25 to 30 units which is a typical length for an oligonucleotide probe required to obtain a stable hybrid. The primary concern regarding length of the PNA-probe is the warranted specificity, i.e. what length is specific enough for that particular application. A 10-mer PNA will typically have a $T_m$ of about 50° C., and a 15-mer typically a $T_m$ of 70° C. with the antiparallel complementary oligonucleotide (DNA or RNA) (Egholm et al. (1993), Nature, 365, 566–568).

Even a 6-mer PNA can form a reasonably stable hybrid with DNA. It has thus been shown that a hybrid formed after mixing a 6-mer PNA T with a 6-mer DNA dA has a $T_m$ of 31° C. (Egholm et al. (1992), J. Am. Chem. Soc. 114, 1895–1897), whereas a hybrid formed after mixing a 6-mer DNA T with a 6-mer DNA dA denatures at a temperature below 10° C.

In contrast to DNA-DNA-duplex formation, no salt is necessary to facilitate and stabilize the formation of a PNA-DNA or a PNA-RNA duplex. The $T_m$ of the PNA-DNA-duplex changes only a little with increasing ionic strength. Typically for a 15-mer, the $T_m$ will drop only 5° C. when the salt concentration is raised from 10 mM NaCl to 1 M NaCl. At low ionic strength (e.g. 10 mM phosphate buffer with no salt added), it is possible to hybridize PNA to a target sequence under conditions where no stable DNA-DNA-duplex formation is able to occur (Nucleic Acid Hybridisation, a practical approach, eds. B. D. Hames & S. J. Higgins, IRL Press 1985, page 62–64). Furthermore, target sites that normally are inaccessible can be made more readily accessible for hybridization with PNA probes at low salt concentration as the secondary and tertiary structure of nucleic acids are melted under such conditions.

Triplex formation with a stoichiometry of 2 PNA and 1 DNA can occur if the PNA-oligomer is very rich in pyrimidines. The stability of such triplexes is extremely high. Typically, a 10-mer homopyrimidine PNA will bind to its target with a $T_m$ in excess of 70° C. as compared to 23° C. for the corresponding $(dT_{10})/(dA_{10})$ complexes (Nielsen et al. (1994), Bioconjugate Chem., 5, 3–7).

The term "naturally occurring nucleobases" includes the four main naturally occurring DNA bases (i.e. thymine, cytosine, adenine or guanine) and other naturally occurring nucleobases (e.g. uracil or inosine). Non-naturally occurring nucleobases include modified nucleobases (e.g. nucleobases wherein a label is coupled to the base through a suitable linker).

The strategy for selecting the sequence of the nucleobases of the PNA probes according to the invention is based on a comparison of the available 16S and/or 23S rRNA nucleotide sequence of Neisseria gonorrhoeae and Chlamydia trachomatis to rRNA nucleotide sequences of closely related species and more distantly related bacteria. Regions of rRNA sequences which appear to be different in two closely related species and between the species studied and more distantly related bacteria, so-called species specific sequences, are identified. PNA probes comprising a sufficient number of nucleobases complementary to the target sequence to form stable hybrids between the PNA probe and the target nucleic acid and a sufficient number of nucleobase mismatches to minimize the hybrid formation between the PNA probe and nucleic acid from closely and distantly related species are selected. The utility of PNA probes selected on the basis of these observed nucleotide differences are confirmed by hybridization tests.

This probe selection strategy yields a number of PNA probes useful for identifying Neisseria gonorrhoeae or Chlamydia trachomatis as described hereinafter.

Although it is preferred to use PNA probes targeting species specific rRNA, it will readily be understood that PNA probes complementary to the rRNA targeting probes will be useful for the detection of the genes (DNA) coding for said species specific rRNA. Thus, as used herein, "probes being capable of hybridizing to 16S or 23S rRNA or to the DNA from the area coding for said rRNA" refer to probes hybridizing to sequences in 16S or 23S rRNA or to sequences in the non-coding strand of the rDNA as well as it refers to complementary probes capable of hybridizing to the coding strand of DNA coding for said rRNA sequences.

The length of the PNA probes is optimized for the specific intended use. The optimal length is a function of the distribution of purine and pyrimidine bases and will in contrast to nucleotide probes be less dependent on salt concentration and pH as regulators of the stringency of the hybridization conditions.

The PNA probes according to the present invention may comprise one or more labelling groups connected to the glycine nitrogen for internal labelling of the PNA probes or one or more labelling groups connected to one or both ends of the probe provided that the labelling group does not destroy the performance of the probe. As used herein, the term "label" or "labelling group" means a substituent, which is useful for detecting a probe.

In many instances, it is preferred that the label is attached to the C-terminal and/or N-terminal end of the PNA probe using suitable linkers. Generally, all chemical methods for N- or C-terminal labelling of peptides and for 5' or 3' end labelling of DNA and/or RNA which are presently known may in general terms be applied to PNAs also. Useful labelling groups are defined hereinafter.

For maximum stability, particularly at alkaline pH, the N-terminus of the PNA may be blocked, e.g. with an amino acid such as lysine or glycine. Alternatively, the N-terminus may be modified by a label, an acetyl group or by a saturated or unsaturated aliphatic group, an aromatic group, a heteroaromatic group, a saturated or unsaturated cyclic group and/or a saturated or unsaturated heterocyclic group which may optionally be substituted by one or more heteroatom-containing groups, such as OH, $NH_2$, $SO_2$, SH and COOH. This type of modification prevents gradual intra-molecular rearrangement of the N-terminal residue.

In a preferred embodiment of the invention, the PNA probes may have the general formula (1)

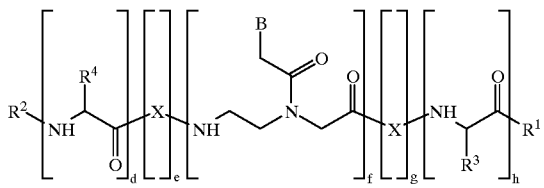

(I)

wherein:
f is an integer from 8 to 20,
each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis,
each X may be identical or different and selected from a group of hydrophilic linker units, and wherein
d is 0 or an integer from 1 to 10,
e is 0 or an integer from 1 to 3,
g is 0 or an integer from 1 to 3,
h is 0 or an integer of 1 to 10,
$R^1$ is OH, $NH_2$, $(X)_q$ or $(X)_q$—L,
$R^2$ is H, $CH_3C(O)$, $(X)_q$ or $(X)_q$—L,
$R^3$ is H, the side chain of a naturally occurring amino acid with the exclusion of Gly, the side chain of a non-naturally occurring alpha amino acid, R'—$(X)_q$ or R'—$(X)_q$—L, wherein R' is the side chain of Thr, Ser, Tyr, Cys, His, Asp, Glu, Lys, Trp, Orn or HomoCys, and
$R^4$ is H, the side chain of a naturally occurring amino acid with the exclusion of Gly, the side chain of a non-naturally occurring alpha amino acid, R'—$(X)_q$ or R'—$(X)_q$—L, wherein R' is the side chain of Thr, Ser, Tyr, Cys, His, Asp, Glu, Lys, Trp, Orn or HomoCys,
and wherein
each L may be identical or different and designate a label, and
q is 0 or an integer from 1 to 20.

In the present context, the term "naturally occurring amino acid" is intended to mean the 20 naturally occurring amino acids. The term "non-naturally occurring amino acid" is intended to mean D-forms of the 20 naturally occurring amino acids, D- and L-forms of Orn, HomoCys as well as other optionally modified alpha amino acids not occurring naturally.

In a further preferred embodiment of the invention, the probes may have the general formula (I) wherein f, B and X are as defined above,
and when
d is 0 or an integer from 1 to 10,
e is 0,
g is 0 or an integer from 1 to 3,
h is 0 or an integer of 1 to 10, then
$R^1$ is OH, $NH_2$, $(X)_q$ or $(X)_q$—L,
$R^2$ is H or $CH_3C(O)$,
$R^3$ is H, the side chain of a naturally occurring amino acid with the exclusion of Gly, the side chain of a non-naturally occurring alpha amino acid, R'—$(X)_q$ or R'—$(X)_q$—L, wherein R' is the side chain of Thr, Ser, Tyr, Cys, His, Asp, Glu, Lys, Trp, Orn or HomoCys, and
$R^4$ is H, the side chain of a naturally occurring amino acid with the exclusion of Gly or the side chain of a non-naturally occurring alpha amino acid,
or when
d is 0 or an integer from 1 to 10,
e is 0 or an integer from 1 to 3,
g is 0,
h is 0 or an integer from 1 to 10, then
$R^1$ is OH or $NH_2$,
$R^2$ is H, $CH_3C(O)$, $(X)_q$ or $(X)_q$—L,
$R^3$ is H, the side chain of a naturally occurring amino acid with the exclusion of Gly or the side chain of a non-naturally occurring alpha amino acid, and
$R^4$ is H, the side chain of a naturally occurring amino acid with the exclusion of Gly, the side chain of a non-naturally occurring alpha amino acid, R'—$(X)_q$ or R'—$(X)_q$—L, wherein R' is the side chain of Thr, Ser, Tyr, Cys, His, Asp, Glu, Lys, Trp, Orn or HomoCys, and each L may be identical or different and designate a label, and q is 0 or an integer from 1 to 20.

In accordance with the present invention in another preferred embodiment, probes may have the general formula (I) wherein f, B, X, L and q are as defined above, and when d is 1, e is 0, g is 0 or an integer from 1 to 3, h is 0 or an integer from 1 to 10, then $R^1$ is OH, $NH_2$, $(X)_q$ or $(X)_q$—L, $R^2$ is H or $CH_3C(O)$, $R^3$ is H or the side chain of a naturally occurring amino acid with the exclusion of Gly, and $R^4$ is H or the side chain of Thr, Ser, Asn, Asp, Glu, Gin, Lys, Arg or His, or when d is 1, e is 0, g is 0 or an integer from 1 to 3, h is an integer of 1 to 10, then $R^1$ is OH or $NH_2$, $R^2$ is H or $CH_3C(O)$, $R^3$ is R'—$(X)_q$ or R'—$(X)_q$—L, wherein R' is the side chain of Thr, Ser, Tyr, Cys, His, Asp, Glu, Lys or Trp, and $R^4$ is H or the side chain of Thr, Ser, Asn, Asp, Glu, Gin, Lys, Arg or His, or when d is 0 or an integer from 1 to 10, e is 0 or an integer from 1 to 3, g and h are 0, then $R^1$ is OH or $NH_2$, $R^2$ is $(X)_q$ or $(X)_q$—L, and $R^4$ is H or the side chain of a naturally occurring amino acid with the exclusion of Gly, or when d is 0 or an integer from 1 to 10, e is 0 or an integer from 1 to 3, g and h are 0, then $R^1$ is OH or $NH_2$, R is H or $CH_3C(O)$, and $R^4$ is R'—$(X)_q$ or R'—$(X)_q$—L, wherein R' is the side chain of Thr, Ser, Tyr, Cys, His, Asp, Glu, Lys or Trp.

PNA probes having the general formula (I) comprise a central core of from 8 to 20 nucleobases (denoted f) of which a sufficient number are nucleobase mismatches to minimize the hybrid formation between the PNA probe and nucleic acid from closely and distantly related species. In some cases, a sequence of as few as 6 nucleo-bases is sufficient to ensure species specificity and the base sequence of the remaining part of the probe is then chosen as complementary to the sequence at the 5' end or 3' end or at both ends of the species specific sequence. Thus, the PNA probes according to the present invention will usually comprise a species specific core sequence and surrounding nucleobases complementary to the target.

As used herein, the term "a species specific sequence" means a sequence comprising a sufficient number of nucleobase mismatches to minimize the hybrid formation between a PNA probe according to the invention and nucleic acid from closely and distantly related species. Thus, a PNA probe according to the invention comprises a sufficient number of nucleobases complementary to the target sequence to form stable hybrids between the PNA probe and the target nucleic acid and a sufficient number of nucleobase mismatches to minimize the hybrid formation between the PNA probe and nucleic acid from closely and distantly related species.

To avoid hydrophobic interaction with the core of the PNA probe, the linker unit X is suitably hydrophilic. When the linker is attached to the C terminus and/or N terminus either directly or via an alpha amino acid, the linker may comprise up to 20 of said linker units. In the PNA probes of formula (I), the linkers, $[X]_g$ and $[X]_e$, may comprise up to 3 of said linker units. Suitable linker units comprise —NH $(CH_2CH_2O)_nCH_2C(O)$—, —NH$(CHOH)_nC(O)$—, —(O)C $(CH_2)_nC(O)$—, —(O)C$(CH_2OCH_2)_nC(O)$— and —NH $(CH_2)_nC(O)$—, wherein n is 0 or an integer from 1 to 6, preferably from 1 to 3. For the purpose of signal amplification, the linker may suitably be a hydrophilic polymer to which one or S more labelling groups may be attached. Particular preferred polymers, such as water-soluble dextrans, are described in WO 93/01498, wherein the labelling group is preferably attached using a divinyl sulfone reagent.

The label L comprises fluorophores, biotin, dinitro benzoic acid, digoxigenin, radio-isotope labels, peptide and enzyme labels, chemiluminiscence label, antigen or antibody labels.

Useful enzyme labels include, but are not limited to, peroxidase, alkaline phosphatase and glucose oxidase. In accordance with the present invention, other examples of useful labels are biotin, 5-(and 6)-carboxyfluorescein, fluorescein isothiocyanate and dinitro benzoic acid as represented by the below-indicated formulas. When a biotin, 5-(and 6)-carboxyfluorescein or fluorescein isothiocyanate label is attached at the N- and/or C-terminal, it is preferred that a linker is incorporated between the PNA and the label.

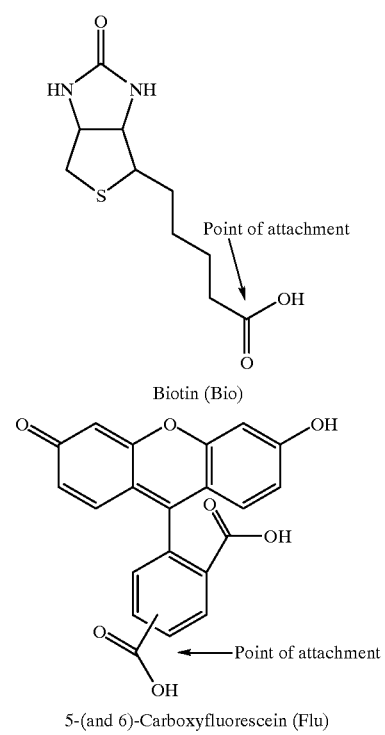

Biotin (Bio)

5-(and 6)-Carboxyfluorescein (Flu)

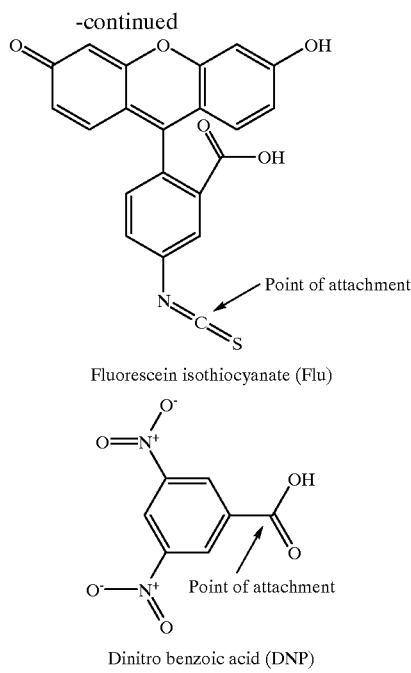

Fluorescein isothiocyanate (Flu)

Dinitro benzoic acid (DNP)

As used in this context, the term "fluorophore" is intended to mean a substance or portion thereof which is capable of exhibiting fluorescence in a detectable range such as 5-(and 6)-carboxyfluorescein, fluorescein isothiocyanate, rhodamine, dansyl and umbelliferone.

The PNA probes having the general formula (I) comprise unlabelled probes and probes labelled at the C-terminal and/or N-terminal. The label might be attached to the side chain of an amino acid selected from the group consisting of Thr, Ser, Tyr, Cys, His, Asp, Glu, Lys, Trp, Orn and HomoCys or the label may be attached directly to the C-terminal and/or N-terminal or it may be attached after introduction of one or more linker units. Alternatively, a labelling of from 1 to 10 of the 20 naturally occurring amino acids (a peptide label) may be attached to the C- and/or N-terminal either directly or after introduction of one or more linker units. It should, however, be understood that in case of probes labelled both in the C-terminal and the N-terminal, the labels may be identical or different.

Unlabelled PNA probes of the general formula (I) are probes wherein the N-terminal amino group may be free or modified by an amino acid selected from the group consisting of Gly and polar amino acids, such as Thr, Ser, Asn, Asp, Glu, Gln, Lys, Arg and His, or the N terminal may be modified by a linker or an acetyl group. The C-terminal of the unlabelled PNA probes having the general formula (I) may be the carboxylic acid or the primary amide thereof from the last N-(2-aminoethyl) glycine unit of the central core of the probe.

Preferred unlabelled PNA probes having the general formula (I) are probes wherein the N-terminal amino group is free or modified by $CH_3C(O)$, lysine or glycine or one or more linker units and the C-terminal is a carboxylic amide group.

Examples of preferred unlabelled PNA probes wherein the C-terminal is an amide group are probes selected among PNA probes having the general formula (I) wherein (a) d is 1, e is 0, g is an integer from 1 to 3, his an integer from 1 to 10, $R^2$ is H, $R^3$ is H or the side chain of a naturally occurring amino acid with the exclusion of Gly, and $R^4$ is H or the side chain of Thr, Ser, Asn, Asp, Glu, Gln, Lys, Arg or His, wherein f, B and X are as defined above;

(b) d, g and h are 0, e is 0 or an integer from 1 to 3 and $R^2$ is $CH_3C(O)$, wherein f, B and X are as defined above;

(c) d is an integer from 1 to 10, e is 0 or an integer from 1 to 3, g and h are 0, $R^2$ is H and $R^4$ is H or the side chain of a naturally occurring amino acid with the exclusion of Gly, wherein f, B and X are as defined above;

(d) d is 1, e, g and h are 0, $R^2$ is H and $R^4$ is H, wherein f and B are as defined above; and (e) d and g are 0, e is 1, h is 0 or 1, $R^2$ is H and $R^3$ is the side chain of Lys, wherein f, B and X are as defined above.

C-terminal labelled PNA probes having the formula (I) may be modified at the N-terminal by one of the following amino acids Gly, Thr, Ser, Asn, Asp, Glu, Gln, Lys, or Arg. One or more labelling groups are attached to the C-terminal amide group or carboxylic acid group, either directly or after introduction of one or more linker units, or the label might be attached to the side chain of an amino acid selected from the group consisting of Thr, Ser, Tyr, Cys, His, Asp, Glu, Lys, Trp, Orn and HomoCys either directly or after introduction of one or more linker units. A peptide label may be attached to the C-terminal of the core of the PNA probe either directly or after introduction of one or more linker units.

Preferred C-terminal labelled PNA probes according to the invention are probes wherein the N-terminal is free or modified by $CH_3C(O)$, lysine or glycine, and the label L is attached to the epsilon amino group of Lys at the C-terminal either directly or after introduction of one or more linker units. Another preferred embodiment are probes wherein the N-terminal amino group is free or modified by $CH_3C(O)$, lysine or glycine and a peptide label of from 1 to 10 of the 20 naturally occurring amino acids is attached either directly or after introduction of one or more linker units to the C-terminal.

Examples of preferred C-terminal labelled PNA probes of formula (I) according to the invention are probes wherein
d and h are 1, e is 0, g is 0 or an integer from 1 to 3, $R^1$ is $NH_2$, $R^2$ is H, $R^3$ is R'—$(X)_q$—L, where R' is the side chain of Lys, and $R^4$ is H or the side chain of Thr, Ser, Asn, Asp, Glu, Gln, Lys, Arg or His, wherein f, B, q, X and L are as defined above.

N-terminal labelled PNA probes having the formula (I) might have a carboxylic acid group or the primary amide thereof at the C-terminal derived from the terminal N-(2-aminoethyl) glycine unit of the central core of the probe. One or more labelling groups are attached to the N-terminal amino group either directly or after introduction of one or more linker units. The N-terminal label might be attached to the side chain of an amino acid selected from the group consisting of Thr, Ser, Tyr, Cys, His, Asp, Glu, Lys, Trp, Orn and HomoCys either directly or after introduction of one or more linker units. A peptide label may be attached to the N-terminal either directly or after introduction of one or more linker units.

Preferred N-terminal labelled PNA probes of formula (I) according to the invention are probes wherein the C-terminal of the terminal N-(2-aminoethyl) glycine unit is a primary amide and the label in the N-terminal is attached either directly or after introduction of one or more linker units. Another preferred embodiment is probes wherein the C-terminal is a primary amide and a peptide label is attached to the N-terminal either directly or after introduction of one or more linker units.

Examples of preferred N-terminal labelled PNA probes of formula (1) according to the invention are probes wherein
d, g and h are 0, e is 0 or an integer from 1 to 3, $R^1$ is $NH_2$ and $R^2$ is L, wherein f, B and L are as defined above.

C- and N-terminal labelled PNA probes having the formula (I) are probes wherein one or more labelling groups are attached to the C- and N-terminal either directly or after introduction of one or more linker units, or through the side chain of an amino acid selected from Thr, Ser, Tyr, Cys, His, Asp, Glu, Lys, Trp, Om and HomoCys either directly or after introduction of one or more labelling units.

Examples of preferred C- and N-labelled probes according to the invention are probes wherein a fluorophore label is attached to the C- and N-terminal either directly or after introduction of one or more linker units. Examples of other preferred C- and N-labelled probes are probes wherein a peptide label is attached to the C- and N-terminal either directly or after introduction of one or more linker units. It should, however, be understood that in some cases, it may be preferred that the labels at the C- and N-terminal are different from each other.

Examples of preferred probes according to the invention are probes of the general formula (Ia) which are probes of the general formula (I) wherein d, e, g and h are 0

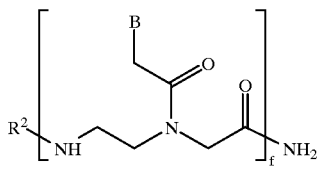
(Ia)

wherein B is as defined above, and wherein f is 20; $R^2$ is $(X)_q$—L, wherein X is —NH(CH$_2$CH$_2$O)$_2$CH$_2$C(O)—; q is 1 or 2 and L is biotin;

f is 18; $R^2$ is $(X)_q$—L, wherein X is —NH(CH$_2$CH$_2$O)$_2$CH$_2$C(O)—; q is 1 or 2 and L is biotin;

f is 18; $R^2$ is $(X)_q$—L, wherein X is —NH(CH$_2$CH$_2$O)$_2$CH$_2$C(O)—; q is 1 or 2 and L is 5-(and 6)-carboxyfluorescein or fluorescein isothiocyanate;

f is 17; $R^2$ is $(X)_q$—L, wherein X is —NH(CH$_2$CH$_2$O)$_2$CH$_2$C(O)—; q is 1 or 2 and L is 5-(and 6)-carboxyfluorescein or fluorescein isothiocyanate;

f is 16; $R^2$ is $(X)_q$—L, wherein X is —NH(CH$_2$CH$_2$O)$_2$CH$_2$C(O)—; q is 1 or 2 and L is biotin;

f is 15; $R^2$ is $(X)_q$—L, wherein X is —NH(CH$_2$CH$_2$O)$_2$CH$_2$C(O)—; q is 1 or 2 and L is 5-(and 6)-carboxyfluorescein or fluorescein isothiocyanate;

f is 15; $R^2$ is $(X)_q$—L, wherein X is —NH(CH$_2$CH$_2$O)$_2$CH$_2$C(O)—; q is 1 or 2 and L is dinitro benzoic acid;

f is 15; $R^2$ is $(X)_3$, wherein $(X)_3$ is HO(O)CCH$_2$C(O)(NH—(CH$_2$CH$_2$O)$_2$CH2C(O))$_2$—; and f is 13; $R^2$ is $(X)_q$—L, wherein X is —NH(CH$_2$CH$_2$O)$_2$CH$_2$C(O)—; q is 1 or 2 and L is 5-(and 6)-carboxyfluorescein or fluorescein isothiocyanate.

The central core of the PNA probes according to the invention is the nucleobase comprising part which is the active part in the hybridization reaction with the nucleic acid target. As mentioned previously, the backbone of the PNA probes according to the invention is structurally homomorphous with the ribose phosphate backbone of traditionally used nucleic acids allowing the Watson Crick basepairing to occur, i.e. T forms basepair with A and C forms basepair with G.

As used herein, a PNA nucleobase sequence of for instance TCG is defined as N-(2-aminoethyl)-N-(thymin-1-ylacetyl)-glycyl linked through an amide bond to the 2-amino group of N-(2-aminoethyl)-N-(cytosin-1-ylacetyl)-glycyl which again is linked through an amide bond to the 2-amino group of N-(2-aminoethyl)-N-(guanin-9-ylacetyl) glycine. To avoid that a base sequence of a PNA probe is mistaken as an oligonucleotide sequence, no sequence list according to the WIPO standard has been included in the present application.

The sequence of nucleobases of preferred PNA probes for detecting Neisseria gonorrhoeae comprises all or part of one of the sequences shown in table 1 or 2, column A or the complementary sequences shown in column B. The base sequences have been selected by comparing sequences published in commonly available databases. PNA probes comprising the sequences shown in column A will identify rRNA sequences or DNA from the non-coding strand of the DNA coding for said rRNA. PNA probes comprising the sequences shown in column B will identify the DNA strand coding for said rRNA.

TABLE 1

Specific sequences for detecting *N. gonorrhoeae*

| A. PNA sequences for detecting 16S rRNA or rDNA (non-coding strand). | B. PNA sequences for detecting 16S rDNA (coding strand). |
|---|---|
| 1a: CCTGTGCTGCCGTCC | 1b: GGACGGCAGCACAGG |
| 2a: CGCTACCC | 2b: GGGTAGCG |
| 3a: CGCCAACCA | 3b: TGGTTGGCG |
| 4a: GGCCGCCGATATTG | 4b: CAATATCGGCGGCC |
| 5a: GCACATGTCAAAA | 5b: TTTTGACATGTGC |

Basepair mismatches to corresponding sequences in N. meningitidis are shown in bold and underlined.

TABLE 2

Specific sequences for detecting *N. gonorrhoeae*

| A. PNA sequences for detecting 23S rRNA or rDNA (non-coding strand). | B. PNA sequences for detecting 23S rDNA (coding strand). |
|---|---|
| 6a: CTTGCA | 6b: TGCAAG |
| 7a: TGCTTCG | 7b: CGAAGCA |
| 8a: GGTAAACC | 8b: GGTTTACC |
| 9a: AATCATA | 9b: TATGATT |

Basepair mismatches to corresponding sequences in N. meningitidis are shown in bold and underlined.

Particularly preferred PNA probes for detecting Neisseria gonorrhoeae comprises all or a part of one of the sequences shown in table 1 or 2, column A.

The specificity of PNA probes comprising all or a part of one of the sequences 1a, 3a, 4a or 5a were tested in a dot blot assay (example 1), a capture ELISA assay (example 2) and in fluorescence in situ hybridization (example 5).

The sequence of nucleobases of preferred PNA probes for detecting Chlamydia trachomatis comprises all or a part of one of the sequences shown in table 3 or 4, column A or the complementary sequence shown in column B. The base sequences have been selected by comparing sequences published in commonly available databases.

TABLE 3

Specific sequences for detecting *C. trachomatis*

| A. PNA sequences for detecting 16S rRNA or rDNA (non-coding strand). | B. PNA sequences for detecting 16S rDNA (coding strand). |
|---|---|
| 10a: CCTTGCGGG | 10b: CCCGCAAGG |
| 11a: GATCTTTGACAA | 11b: TTGTCAAAGATC |
| 12a: CAGCGGG | 12b: CCCGCTG |
| 13a: ACCGCCT | 13b: AGGCGGT |
| 14a: TAGCTGATATCA | 14b: TGATATCAGCTA |
| 15a: CGTTACTCG | 15b: CGAGTAACG |
| 16a: CAAATATCG | 16b: CGATATTTG |
| 17a: AAGGACAA | 17b: TTGTCCTT |
| 18a: CAATTGCC | 18b: GGCAATTG |
| 19a: ACAATTGCT | 19b: AGCAATTGT |
| 20a: CGACTC | 20b: GAGTCG |

Basepair mismatches to corresponding sequences in both C. psittaci and C. pneumoniae are shown in bold and are underlined. C. psittaci and C. pneumoniae are closely related to C. trachomatis. Differences to only one of the species have not been indicated.

TABLE 4

Specific sequence for detecting *C. trachomatis*

| A. PNA sequences for detecting 23S rRNA or rDNA (non coding strand) | B. PNA sequences for detecting 23S rDNA (coding strand). |
|---|---|
| 21a: CTATCGTTCCATAG | 21b: CTATGGAACGATAG |
| 22a: TCTTTGCTTATCAC | 22b: GTGATAAGCAAAGA |
| 23a: TCAGCATGCAAT | 23b: ATTGCATGCTGA |
| 24a: GTCGCTTTGCATACC | 24b: GGTATGCAAAGCGAC |
| 25a: GAGCCTTATCAGCTC | 25b: GAGCTGATAAGGCTC |
| 26a: TAGGAGTCCTGA | 26b: TCAGGACTCCTA |
| 27a: TGTTGAGGTCGG | 27b: CCGACCTCAACA |
| 28a: CTTGATCGCGACCTGAT | 28b: ATCAGGTCGCGATCAAG |
| 29a: TTCTCATCGCTCTACGGACTC | 29b: GAGTCCGTAGAGCGATGAGAA |
| 30a: TGTCTTATCGAC | 30b: GTCGATAAGACA |
| 31a: CTTTATCCTCAAT | 31b: ATTGAGGATAAAG |
| 32a: CTTTCTCTCCTT | 32b: AAGGAGAGAAAG |
| 33a: AGTCTATTACTC | 33b: GAGTAATAGACT |

Basepair mismatches to corresponding sequences in C. psittaci are shown in bold and are underlined. C. psittaci is closely related to C. trachomatis.

Particularly preferred PNA probes for detecting Chlamydia trachomatis comprise all or a part of one of the sequences shown in table 3 or 4, column A.

The specificity of PNA probes comprising all or a part of one of the sequences 11a, 13a, 15a or 18a were tested in a capture ELISA assay (example 4).

The preferred length of the probe will vary in accordance with the length of the species specific sequences and the number of mismatches of basepairs. The probe will usually comprise from 8 to 20 nucleobases, preferably from 12 to 20 nucleo-bases and most preferably from 12 to 17 nucleo-bases. The label is preferably 5-(and 6)-carboxyfluorescein, fluorescein isothiocyanate, dinitro benzoic acid or biotin, which is attached to the probe by a linker consisting of 2 units of $—NH(CH_2CH_2O)_2CH_2C(O)—$. The probe is constructed so that the mismatch of basepairs compared to closely related species preferably is located central in the probe.

The PNA probes according to the invention may be synthesized by adaption of standard peptide synthesis procedures, either in solution or on solid phase. The synthons used may be specially designed monomer amino acids or their activated derivatives, protected by standard protecting groups.

Preferred monomer synthons for synthesis of both labelled and unlabelled probes according to the invention are PNA monomers protected with t-butoxycarbonyl14benzyloxycarbonyl— (Boc—/Z—). Alternatively, PNA could be synthesized using Fmoc (9-flurenylmethyloxycarbonyl) protected monomers. The Boc—/Z—PNA monomers used have the formulas (II) to (V):

(II)

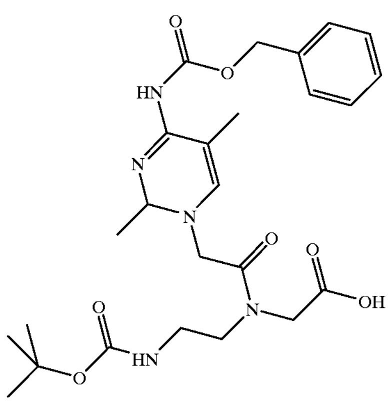

Boc-C$^{z}$aeg-OH (III)

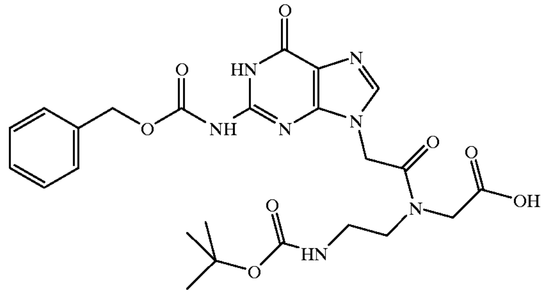

Boc-G$^{z}$aeg-OH

-continued (IV)

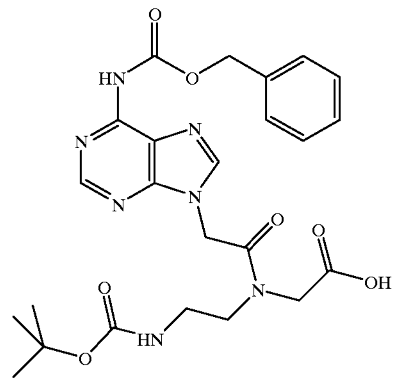

Boc-A$^{z}$aeg-OH (V)

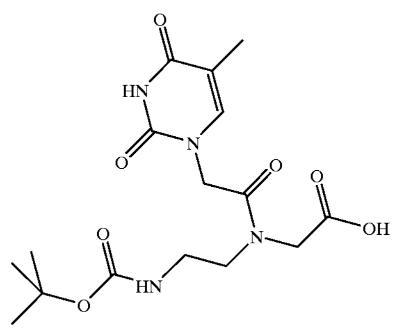

Boc-Taeg-OH wherein the following terms are defined as follows:

aeg: N-(2-aminoethyl)glycine

Boc: t-butoxycarbonyl

Z: benzyloxycarbonyl

A: Adenine

G: Guanine

C: Cytosine

T: thymine

The PNAs according to the invention were synthesized according to the procedures described in "PNA Information Package" obtained from Millipore. Polyethyleneglycol-polystyrene (PEG-PS) support derivatized with a benzhydrylamine-linker was used as resin for synthesis of C-terminal amidated PNAs. This PEG-PS resin is preferred as it solvates the growing PNA chain much better than the commonly used methylbenzylhydrylamine (MBHA) resin and thereby facilitating rapid acylation of the N-terminal amino group. The PNA monomers dissolved together with a tertiary amine was activated with O-(7-azabenzotriazole-1-yl)-1,1,3,3-tetramethyluronium hexafluorophosphate (HATU). This activation reagent improves the coupling efficiencies, in particular in cases of a difficult coupling step. For capping of non-acylated N-terminal amino groups, $N^1$-benzyloxycarbonyl-$N^3$-methylimidazole (NBCMIT, Rapoport's reagent) or acetic anhydride was used. The previously described preferred linkers were incorporated at the N-terminal end of the PNA using standard solid phase peptide chemistry.

Preferred protection groups for the amino function of the previously described linkers are Fmoc and Boc. For incorporation of amino acids, the Fmoc amino acids were used. Both the linker and the amino acids were activated with HATU. When using the Fmoc strategy for elongation of the PNA chain with linkers or amino acids, it was possible to have side chains amino groups protected with acid sensitive protection groups such as the Boc group. This method allows introduction of a linker containing several Boc protected amino groups which can all be cleaved and labelled in the same synthesis cycle.

One way of labelling PNA was to use 5-(and 6)-carboxyfluorescein protected on both hydroxyl groups with an acid sensitive protection group. The remaining acid group was activated with HATU and reacted with the N-terminal amino group in the linked or non-linked PNA chain. The same technique can be applied to other labelling groups containing an acid function.

The PNAs was cleaved from the resin with trifluoromethane sulfonic acid (TFMSA) in m-cresol and TFA.

The PNA oligomers synthesized are purified by reversed-phase HPLC at 50° C. To ensure the quality of the product, the PNAs can be analyzed by reversed-phase HPLC and characterized by plasma desorption mass spectrometry (PDMS) or electron spray mass spectrometry (ESMS).

UV absorption at 260 nm can be used to quantitate the PNA oligomers, but the absorption should be measured at temperatures higher than 50° C. as a single stranded PNA oligomer appears to have secondary structures at room temperature. Most single stranded PNA shows a sigmoidal melting curve with a $T_m$ of 40–45° C. practically independent of the sequence and length at the PNA oligomer.

The probes according to the invention are used in the detection of Neisseria gonorrhoeae or Chlamydia trachomatis in samples which may contain these bacteria.

In the assay method at least one PNA probe according to the invention is contacted with target nucleic acid and an analysis for hybrid formation is carried out.

In the assay method according to the invention, a sample to be analysed for a sexual transmitted disease is contacted with (a) one or more PNA probe comprising a sequence which is specific for Neisseria gonorrhoeae as defined above, and/or (b) one or more PNA probe comprising a sequence which is specific for Chlamydia trachomatis as defined above under conditions such that hybridization between the PNA probe and any complementary sample rRNA or the genome sequences coding for said rRNA of Neisseria gonorrhoeae or Chlamydia trachomatis can occur, and observing or measuring the resulting hybridization.

In one embodiment of the assay method, conventionally prepared smears of bacterial cells are contacted with one or more PNA probes according to the invention under conditions suitable for hybridization to occur between the PNA probe(s) and any complementary rRNA in the sample. The complexes formed are detected. An example of this assay format is fluorescence in situ hybridization (FISH) wherein the PNA probes according to the invention are labelled with fluorescein or another fluorophore.

In another embodiment of the assay method, a test sample is first subjected to conditions which release nucleic acid from the bacteria present in that sample. Contact between one or more PNA probes according to the invention, which may be labelled, and the rRNA or rDNA target may be carried out in solution under conditions which promote hybridization between the PNA probe and any target nucleic acid present. The PNA-nucleic acid complex may be immobilised to a solid support, for instance by using a capture probe or a catching antibody specific for PNA-nucleic acid complexes as described in PCT/DK94/00483.

Due to the high affinity of PNA for nucleic acid, it is not necessary to carry out the hybridization of PNA and nucleic acid in solution. This allows flexibility in the assay format. For instance, the PNA detection probes can be contacted with the target nucleic acid in solution and the PNA-nucleic acid complex can be captured by an immobilised capture probe. Or the sample comprising the target nucleic acid can even be added to an assay system comprising detection probes as well as immobilised capture probe. The immobilisation of the capture probe might be effected by using a streptavidin coated solid phase and a biotinylated capture probe. The PNA probe may be immobilised onto a solid support by coupling reaction between a carboxylic acid on the linker and an amino derivatized support. Alternatively, the coupling onto the solid support may be accomplished by photochemical activation of photoreative groups which have been attached absorptively to the solid support prior to photochemical activation. Such photoreactive groups are described in EP-A 408 078.

In practice, a solid phase based assay system is very attractive as the analysis can be carried out using a solid phase precoated with a capture probe. A solid phase based assay system is also feasible for automatization of the analysis.

The capture probe may be one of the other species specific PNA probes not used in the hybridization reaction for detecting the target nucleic acid thus ensuring dual species specificity. PNA capture probes are preferred over oligonucleotides as PNA, in contrast to oligonucleotides, is not attacked by nucleases which may be present in the sample.

The solid support may take a wide variety of forms as is known in connection with immobilisation of oligonucleotides for use in affinity capture. A solid support may, for instance, be a plate, a multi-well plate, a microscope slide, a filter or a dip stick. It may take the form of individual particles such as magnetic beads.

It has been observed that PNA binds to a variety of solid phases. A blocking reaction is required to reduce unspecific binding of PNA to the solid phase. The blocking reaction may be carried out with commonly used blocking reagents, such as BSA, casein, Triton X-100 or Tween 20. The preferred blocking reagents are Triton X-100 and Tween 20.

The captured PNA-nucleic acid complex may be detected or identified by a wide variety of methods. The PNA probe reacted with target nucleic acid may be labelled whereby said label may form part of the detection system. In another embodiment, the captured PNA-nucleic acid complex is detected using a detection system based on an antibody reacting specificly with PNA-nucleic acid complexes, in which detection system the primary antibody against PNA-nucleic acid complexes might comprise a label, or which detection system comprises a labelled secondary antibody, which specifically binds to the primary antibody.

The present invention further includes kits for use in diagnostics incorporating at least one PNA probe according to the invention and at least one detection reagent. When the PNA probe to be contacted with target nucleic acid is labelled, at least one detection reagent for use in detecting said label is included.

Generally, the PNA probes will be provided in solution in a hybridization buffer. Such a kit will generally also include at least one washing buffer solution. If an enzyme label is used, the kit may comprise a substrate for the enzyme, which is suitable to undergo a monitorable reaction mediated by the enzyme.

To increase the sensitivity, an amplification system can be employed in the detection system of PNA-nucleic acid complexes. Suitable amplification systems are the water-soluble conjugates described in WO 93/01498, for instance water soluble dextrans, to which are attached antibody molecules that specifically recognize a PNA-nucleic acid complex and detectable labels. Another suitable amplification system is an enzyme cycling system (AMPAK) designed to amplify the colorometric signal generated by alkaline phosphatase labels (Johannsson, A. and Bates, D. L. (1988). Amplification by Second Enzymes. In: ELISA and Other Solid Phase Immunoassays (eds. D. M. Kemeny and S. J. Challacombe). John Wiley & Sons Ltd, pp 86–106). Bound enzyme converts NADPH in the substrate into NADH. This acts as the essential cofactor in the subsequent amplifier cycling step. A typical amplifier comprises two enzymes that catalyse the redox cycle which interconverts NADH and NAD. For each turn of the cycle, a molecule of coloured product is generated. Hence the signal from the primary enzyme is amplified many times.

The invention is illustrated by the following examples.

EXAMPLE 1

Dot blot assay

To test the sensitivity and specificity of PNA probes according to the invention, four representative PNA oligomers (PNA-1, PNA-3, PNA4, and PNA-5) complementary to specific parts of N. gonorrhoreae 16S rRNA were selected and synthesized. These sequences, as indicated in table 5, were labelled with either 5-(and 6)-carboxyfluorescein or biotin. A "synthetic DNA target sequence" ("62-mer" in table 5) complementary to three of the PNA oligomers (PNA-1, PNA-3, and PNA4), and thus containing three sequence stretches of N. gonorrhoeae 163 rRNA sequences, were synthesized. Also, another "synthetic DNA target sequence" ("61-mer" in table 5) complementary to the analogous stretches in N. meningitidis 16S rRNA, were synthesized. Sequence differences between the 62- and 61-mer are indicated with bold letters in both sequences.

Prehybridization: Each filter were sealed into a plastic back a covered with 10 mM Phosphate buffer, pH 7.0, 100 mM NaCl, and 0.5% Casein. Incubation was carried out for 60 minutes at 65° C. After incubation the plastic back was opened and prehybridization solution was squeezed out.

Hybridization: 50 ng/ml of PNA oligomer (or 50 ng of each oligomer) in hybridization solution as above were added to the plastic back and incubated over night at 50° C.

Post hyb. wash: The filters were washed 4×15 minutes at room temp. in 2×SSC, 0.1% SDS.

Visualisation: Bound Flu-labelled probes are visualised following standard protocols using either Rabbit(Fab') anti-FITC (fluorescein isothiocyanate)/AP (0.1 µg/ml) or, for the filter hybridized with Bio-PNA4, Streptavidin/AP (0.4 µg/ml). After incubation and washing a NBTIBCIP substrate solution was added and the filters were incubated 2 hours at room temperature, washed and dried.

TABLE 6

Sensitivity of individual PNA probes in dot-blot assay

| PNA probe | Gonococci RNA | 62-mer | 61-mer | E. Coli rRNA |
|---|---|---|---|---|
| PNA-1 (Flu) | 0.04 µg | 0.2 µg | neg. | neg. |
| PNA-3 (Flu) | 0.04 µg | 0.04 µg | 0.2 µg | neg. |
| PNA-4 (Bio) | 0.04 µg | 0.2 µg | neg. | neg. |
| PNA-5 (Flu) | 0.2 ug | neg. | neg. | neg. |
| Mix of PNA-1, -3, and -5 | 0.008 µg | 0.008 µg | 1.0 µg | neg. |

Numbers given is the amount of RNA dotted on the filter and visualisable with the indicated probes.

Conclusion: Generally, the PNA oligomers synthesized recognises N. gonorrhoeae RNA as well as the N. gonor-

TABLE 5

PNA and DNA sequences used

| | | |
|---|---|---|
| PNA-1 | Flu-X-tcCCTGTGCTGCCGTCC-NH$_2$ | (derived from 1a) |
| PNA-3 | Flu-X-acccCGCCAACCAgcta-NH$_2$ | (derived from 3a) |
| PNA-4 | Bio-X-cGGCCGCCGATATTGgcaac-NH$_2$ | (derived from 4a) |
| PNA-5 | Flu-X-tccGCACATGTCAAAAcc-NH$_2$ | (derived from 5a) |
| 62-mer (SEQ. ID NO. 1) | 5'-GGACGGCAGCACAGGGATCGATAGCTGGTTGGCGGGGTGACTGTTGCCAATATCGGCGGCCG-3' | |
| 61-mer (SEQ. ID NO. 2) | 5'-GGCCGCAGCACAGAGATCGATAGCTAGTTGGTGGGGTGACTGTTGCTAATATCAGCGGCTG -3' | |

Small letters in the sequences denote nucleobases complementary to the target but not included in the sequence of table 1 from which the probes are derived.

N. gonorrhoeae bacterial cells were spread out on a chocolate agar plate. The plate was incubated over night at 37° C. Total RNA was isolated from the bacterial cells either by a standard protocol using guanidinium isothiocyanate (Maniatis et al., Molecular Cloning, A Laboratory Manual, 2nd edition, 1989) or by the use of Qiagen's "RNeasy Total RNA Kit". E. coli rRNA was purchased from Boehringer Mannheim.

1000, 200, 40, 8, and 1.6 ng total N. gonorrhoeae RNA, 62-mer, 61-mer, and E. coli rRNA were dotted on Nylon filters and each filter was hybridized with one of the different detection and capture PNA probes, or with the three Flu-labelled PNA probes, as described below.

rhoeae related 62-mer DNA sequence but not the N. meningitidis related 61-mer DNA sequence. PNA-3 also gives rise to a weak signal with the 61-mer sequence representing N. meningitidis. More stringent conditions are probably needed in such a filter hybridization assay in order to achieve absolute specificity with the PNA-3 probe as well.

EXAMPLE 2

To test the performance of PNA oligomers in a capture ELISA assay, the positive (62-mer) and negative (61-mer) target sequences representing N. gonorrhoea and N. meningitidis, respectively, were used together with the individual PNA oligomers previously described. Target sequence and probes are allowed to hybridize and the resulting complex is captured in a streptavidin-coated ELISA well. Captured complex is visualised via the Flu-label attached to the capture probes using e.g. an Alkaline Phosphatase (AP) conjugated Fab' fragment (Rabbit (Fab') anti-FITC/AP) isolated from a rabbit polyclonal antibody preparation. Bound conjugate is visualised using p-nitro phenyl phosphate (PNPP).

Signal amplification systems based on e.g. rabbit anti-FITC antibody and AP conjugated to a water soluble dextran polymer (WO 93101498) as well as the enzyme cycling system, AMPAK, (Johannsson, A. and Bates, D. L. (1988). Amplification by Second Enzymes. In: ELISA and Other Solid Phase Immunoassays (eds. D. M. Kemeny and S. J. Challacombe). John Wiley & Sons Ltd, pp 86–106) is exemplified can be used.

Standard capture ELISA Assay

Unless otherwise mentioned the standard ELISA protocol given below were followed during our capture ELISA assay.

1. Hybridization of probes and target sequence was performed in an eppendorf tube in a total volume of 100 µl containing:
   10 mM Sodium Phosphate, pH 7.0 100 mM NaCl
   x ng/well 62-mer Target sequence(e.g. x=50, 25, 12.5, 6.25, 3.13, 1.56, or 0)
   50 ng/well of Capture probe (PNA4)
   50 ng/well of each Detection probe (PNA-1 and PNA-3)
   Incubated at 50° C. for one hour.
2. The hybridization solution was transferred to an ELISA well and incubated at 50° C. for one hour.
3. The wells were washed three times with THT-buffer using a standard ELISA-washer.
4. 100 µl of antibody conjugate was added to each well and incubated with shaking at 37° C. for 30 minutes.
5. The wells were washed three times with THT-buffer using a standard ELISA-washer.
6. 100 µl of freshly prepared PNPP in substrate buffer was added to each well and incubated with shaking at 37° C. for 15–30 minutes.
7. The colour development was stopped by the addition of 100 µl 0.5 N NaOH.
8. Generated colour was registered by measuring the absorbency at $OD_{405}$ using a standard ELISA-plate reader.

Buffers and chemicals used are described further below:

THT-buffer: 50 mM Tris-HCl, pH 7.2 100 mM NaCl 0.1% Tween-20

Antibody solution: Rabbit(Fab') anti-FITC (fluorescein isothiocyanate)/AP (0.2 mg/ml) were diluted 1:20 in THT.

Substrate Buffer: 1 M Diethanolamine, pH 9.8 0.5 mM $MgCl_2$

PNPP: Three tablets of p-Nitrophenyl phosphate (PNPP, e.g. Sigma product no. 104–105, 5 mg/tablet) were added to 15 ml of the above described "Substrate Buffer"

Modifications in relation to the standard protocol previously described are indicated below:

1. Four hybridization mixtures were made:
   (1) 5 ng of the N. gonorrhoea related 62-mer DNA sequence as target was mixed with capture probe and detection probes as described above.
   (2) 5 ng of the N. meningitidis related 61-mer DNA sequence as target was mixed with capture and detection probes as described above.
   (3) Capture and detection probes as described above (no target sequence).
   (4) Blank (=Hybridization Buffer).
6. Substrate incubation were allowed to proceed for 15 minutes.

Results are shown in table 7.

TABLE 7

PNA probes in capture ELISA assay

| | $mOD_{405}$ |
|---|---|
| 62-mer | 1500 |
| 61-mer | 100 |
| No target | 100 |
| Buffer Blank | 50 |

Results: The signals obtained show that the biotinylated PNA-4 probe is able to capture the 62-mer target sequence. Also, PNA-1 and -3 are able to hybridize to their target sequence as well as to bind the antibody conjugate resulting in a strong signal in the assay.

Conclusion: PNA probes perform well as capture and detection probes in this capture ELISA assay with a high degree of specificity.

EXAMPLE 3

Comparison of PNA and DNA probes in a capture ELISA assay

To compare the sensitivity of PNA versus DNA oligomers as capture and detection probes, the following experiment was made. DNA probes with the same base sequence and label as PNA-1, PNA-3, and PNA-4 were synthesized.

Modifications in relation to the standard capture ELISA protocol are indicated below:

1. Target 62-mer in a dilution row (x=50, 25, 12.5, 6.25, 3.13, 1.56, or 0) was mixed in eppendorf tubes with capture and detection PNA or DNA probe mixtures. Reaction time for the hybridization was, in this experiment, reduced to 15 minutes.
2. Capture time was reduced to 15 minutes.
6. Substrate incubation was allowed to proceed for 30 minutes.

Results are given in table 8.

TABLE 8

Comparison of PNA and DNA probes

| ng 62-mer in each well | PNA probes $mOD_{405}$ | DNA probes $mOD_{405}$ |
|---|---|---|
| 50 | 2300 | 210 |
| 25 | 1750 | 150 |
| 12, 5 | 1340 | 110 |
| 6, 25 | 910 | 80 |
| 3, 125 | 550 | 70 |
| 1, 56 | 310 | 50 |
| 0 | 70 | 50 |
| Blank | 40 | 40 |

Results: This experiment was designed to compare the ability of PNA and DNA probes to function as capture and detection probes in a fast assay set-up (15 minutes hybridization, 15 minutes capture).

Conclusions: This experiment shows that PNA oligomers are able to hybridize much faster than DNA oligonucleotides resulting in a stronger signal with the PNA oligomers as compared to when the corresponding DNA oligonucleotides are used.

EXAMPLE 4

Capture ELISA test of C. trachomatis rRNA

A cell culture was infected with a C. trachomatis strain and grown over night at 37° C. Total RNA were isolated using a standard protocol with guanidinium isothiocyanate (Maniatis et al., Molecular Cloning, A Laboratory Manual, 2nd edition, 1989). This RNA preparation will contain both human and bacterial total RNA. As a control, total RNA was isolated from an uninfected cell culture using the same procedure.

Four representative PNA oligomers complementary to specific regions of C. trachomatis 16S rRNA were selected and synthesized. Synthesized sequences and labels added are shown in table 9. The capture probe (PNA-11) was labelled with biotin and the three detection probes (PNA-12, -13, and -14) were labelled with dinitro benzoic acid (DNP).

TABLE 9

PNA oligomers complementary to C. trachomatis 16S rRNA

| PNA-11 | Bio-X-acAATTGCCgaaacaat-$NH_2$ | (derived from 11a) |
| PNA-12 | DNP-X-aaCGTTACTCGgatg-$NH_2$ | (derived from 12a) |
| PNA-13 | DNP-X-gtaTTAACCGCCTtc-$NH_2$ | (derived from 13a) |
| PNA-14 | DNP-X-ccGATCTTTGACaac-$NH_2$ | (derived from 14a) |

Small letters in the sequences denote nucleobases complementary to the target but not included in the sequence of table 3 from which the probes are derived.

Modifications in relation to the standard capture ELISA protocol are indicated below:
1. A dilution row of the target total RNA (x=100, 25, 5, 1, and 0) was mixed in eppendorf tubes with capture and detection PNA probes.
4. 100 μl of antibody conjugate (Rabbit(Fab') anti-DNP/ AP conjugate) was added to each well and incubated with shaking at 37° C. for 30 minutes.
6. Substrate incubation was allowed to proceed for 15 minutes. Results are given in table 10.

TABLE 10

Detection of C. trachomatis infected cells

| ng RNA in assay | Total RNA from infected cells $mOD_{405}$ | Total RNA from uninfected cells $mOD_{405}$ | Total RNA from N. gonorrhoeae $mOD_{405}$ |
|---|---|---|---|
| 100 | 1110 | 390 | 330 |
| 25 | 770 | 270 | 200 |
| 5 | 330 | 200 | 140 |
| 1 | 170 | 180 | 100 |
| 0 | 90 | 90 | 90 |

Results: Also labelling of PNA oligomers with the hapten DNP functions well, both during synthesis and in the capture ELISA assay. The signal obtained with RNA purified from C. trachomatis infected cells is significantly higher than the signal obtained with RNA purified from uninfected cells. The signal obtained using RNA purified from N. gonorrhoeae is as low as the signal obtained from uninfected cells.

Conclusions: PNA oligomers perform well as capture and detection probes for the detection of C. trachomatis 16S rRNA

EXAMPLE 5

In situ hybridization to fixed bacterial cells

To further test the ability of PNA oligomers to distinguish between different Niesseria strains, fluorescence in situ hybridization (FISH) on fixed bacterial cells using Flu-labelled PNA probes as indicated below was performed. The use of fluorescent anti-bodies or DNA probes for the visualization of bacteria in cell smears is a technology well known in the art.

Protocol for FISH on bacterial cells

Preparation of bacterial slides.

Bacterial cells of interest are plated out on suitable agar plates and incubated over night at recommended conditions (the different Neisseria strains were plated out on chocolate agar plates incubated at 37° C. in an incubator with additional 5% $CO_2$).

Bacterial smears were prepared on test slides according to standard procedures. The smears were air-dried followed by flame fixation.

FISH on bacterial slides.
1. The bacterial slide is covered with a hybridization solution containing PNA probe or probe mixture (each probe at a concentration of 50–100 ng/ml).
2. Incubated in an humid incubation chamber at 55° C. for 60 minutes.
3. Washed 2×15 minutes with shaking in TBS-buffer, pH 9.0 at 55° C.
4. The slide is dried and mounted "DAKO Fluorescence Mounting Medium" or equivalent.

Hybridization solution: 1×PE-buffer:
10 mM NaCl
10% Dextran Sulphate
30% Formamide
0.1% Triton X-100
10×PE-buffer:
500 mM Tris-HCl, pH 7.6
50 mM EDTA
1% Sodium pyrophosphate
2% Polyvinylpyrrolidone
2% Ficol
10×TBS buffer:
100 mM Sodium phosphate, pH 7.2
1.45 M NaCl All solutions are made RNase free following standard procedures.

TABLE 11

Neisseria strains tested by FISH

| Bacteria | Strain | FISH |
|---|---|---|
| N. gonorrhoeae | 190/94 | Positive |
| N. gonorrhoeae | Engl. 6988 | Positive |
| N. gonorrhoeae | KI WHO A | Positive |
| N. gonorrhoeae | KII WHO C | Positive |
| N. gonorrhoeae | KIV WHO D | Positive |
| N. meningitidis | M 1027 | Negative |
| N. meningitidis | H 44 | Negative |
| N. meningitidis | C11 | Negative |

Results: FISH was performed as described above. A mixture of two 15-mer versions of PNA-1 and PNA-3 were used as probes (PNA-1.1: Flu-X-X-cCCTGTGCTGCCGTC-$NH_2$ (derived from 1a) and PNA-3.1: Flu-X-X-CCCCGCCAACCAgct-$NH_2$ (derived from 3a)). Small letters in the sequences denote nucleobases complementary to the target but not included in the sequence of table 1 from which the probes are derived. Slides were evaluated blindly in fluorescence microscope.

Conclusions: The PNA oligomers perform well as detection probes in this fluorescence in situ hybridization assay. The probes gives positive results with all five N. gonorrhoeae strains tested and simultaneously negative reactions (only autofluorescence) with all three N. meningitidis strains.

The feasibility of the PNA probes according to the invention for use in detection of Neisseria gonorrhoeae and/or Chlamydia trachomatis has been shown in examples 1 to 5.

Treatment of samples. A biological sample suspected for containing Neisseria gonorrhoeae and/or Chlamydia trachomatis (e.g. a cervical swab or an urine sample) is transferred to a suitable "transport solution". A person skilled in the art will know how to select a suitable transport solution in which the bacteria are permeabilized and the RNA is protected against nucleases.

Analysis of bacteria samples. The samples suspected to contain Neisseria gonorrhoeae and/or Chlamydia trachomatis may be analysed as described above. The species specificity is particularly tested against the closely related species but also against more distant related species.

The most closely related species to N. gonorrhoeae to be expected in the samples is N. meningitidis.

The most closely related species to C. trachomatis to be expected in the samples are C. pneumoniae and C. psittaci.

We claim:

1. A method of detecting a sexually transmitted disease caused by Neisseria gonorrhoeae or Chlamydia trachomatis comprising contacting a rRNA or DNA molecule containing sample from a cell sample suspected of containing said rRNA or DNA with a peptide nucleic acid hybridization probe of formula 1, under conditions such that hybridization between said peptide nucleic acid probe and any complementary sample rRNA or DNA sequences coding for said rRNA of Neisseria gonorrhea or Chlamydia trachomatis in said sample, can occur, and detecting binding between said peptide nucleic acid probe and said rRNA or DNA in said sample as indication of presence of said Neisseria gonorrhea or Chlamydia trachomatis in said sample, wherein said peptide nucleic acid probe is specific for one of Neisseria gonorrhea or Chlamydia trachomatis; and

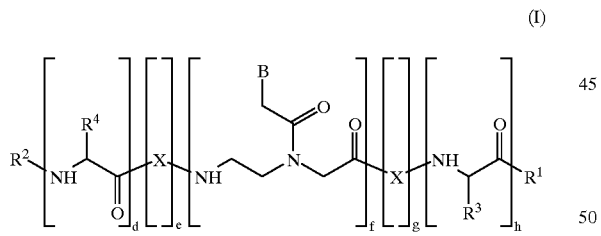

(I)

wherein f is an integer from 6-30, each B is selected from the group consisting of the nucleobases thymine, adenine, cytosine, guanine, and uracil, and non-naturally occurring nucleobases, in a sequence enabling the probe to hybridize to 16S or 23S rRNA or DNA sequences from the area coding for said rRNA of Neisseria gonorrhea or Chlamydia trachomatis, each X may be identical or different and selected from a group of hydrophilic linker units, independently selected among —NH(CH$_2$CH$_2$O)$_n$CH$_2$C(O)—, —NH(CHOH)$_n$C(O)—, —(O)C(CH$_2$)$_n$C(O)—, —(O)C(CH$_2$OCH$_2$)C(O)— and —NH(CH$_2$)$_n$C(O)—, wherein n is 0 or integer from 1 to 6, preferably and integer from 1 to 3, and wherein d is 0 or an integer from 1 to 10, e is 0 or an integer from 1 to 3, g is 0 or an integer from 1 to 3, h is 0 or an integer from 1 to 10, $R^1$ is OH, NH$_2$ (X)$_q$—L, $R^2$ is H, CH$_3$C(O), (X)$_q$—L, $R^3$ is H, the side of a naturally occurring amino acids with the exclusion of Gly, the side chain of a non-naturally occurring alpha amino acid, R'—(X)$_q$ or R'—(X)$_q$—l, wherein R' is the side chain of Thr, Ser, Tyr, Cys, His, Asp, Glu, Lys, Trp Orn, or HomoCys, and $R_4$ is H, the side chain of a naturally occurring amino acid with the exclusion of Gly, the side chain of a non-naturally occurring alpha amino acid, R'—(X)$_q$ or R'—(X)$_q$—l, wherein R' is the side chain of Thr, Ser, Tyr, Cys, His, Asp, Glu, Lys, Trp, Orn, or HomoCys, and wherein each L may be identical or different and designate a label, and q is 0 or an integer from 1 to 10.

2. The method according to claim 1, wherein said probe comprises a sufficient number of nucleobases complementary to the target sequence to form stable hybrids between the PNA probe and the target nucleic acid and a sufficient number of nucleobase mismatches to minimize the hybrid formation between the PNA probe and nucleic acid from closely and distantly related species.

3. The method according to claim 2, wherein said probe comprises from 8 to 20 N-(2-aminoethylglycine) units.

4. The method according to claim 1, wherein f is an integer from 8 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, each X may be identical or different and selected from a group of hydrophilic linker units, and when d is 0 or an integer from 1 to 10, e is 0, g is 0 or an integer from 1 to 3, h is 0 or an integer of 1 to 10, then $R^1$ is OH, NH$_2$, (X)$_q$ or (X)$_q$—L, $R^2$ is H or CH$_3$C(O), $R^3$ is H, the side chain of a naturally occurring amino acid with the exclusion of Gly, the side chain of a non-naturally occurring alpha amino acid, R'—(X)$_q$ or R'—(X)$_q$—L, wherein R' is the side chain of Thr, Ser, Tyr, Cys, His, Asp, Glu, Lys, Trp, Orn or HomoCys, and $R^4$ is H, the side chain of a naturally occurring amino acid with the exclusion of Gly or the side chain of a non-naturally occurring alpha amino acid, or when d is 0 or an integer from 1 to 10, e is 0 or an integer from 1 to 3, g is 0, h is 0 or an integer from 1 to 10, then $R^1$ is OH or NH$_2$, $R^2$ is H, CH$_3$C(O), (X)$_q$ or (X)$_q$—L, $R^3$ is H, the side chain of a naturally occurring amino acid with the exclusion of Gly or the side chain of a non-naturally occurring alpha amino acid, and $R^4$ is H, the side chain of a naturally occurring amino acid with the exclusion of Gly, the side chain of a non-naturally occurring alpha amino acid, $R'$—$(X)_q$ or $R'$—$(X)_q$—L, wherein R' is the side chain of Thr, Ser, Tyr, Cys, His, Asp, Glu, Lys, Trp, Orn or HomoCys, and each L may be identical or different and designate a label, and q is 0 or an integer from 1 to 20.

5. The method according to claim 1, wherein f is an integer from 8 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, each X may be identical or different and selected from a group of hydrophilic linker units, and when d is 1, e is 0, g is 0 or an integer from 1 to 3, h is 0 or an integer from 1 to 10, then $R^1$ is OH, $NH_2$, $(X)_q$ or $(X)_q$—L, $R^2$ is H or $CH_3C(O)$, $R^3$ is H or the side chain of a naturally occurring amino acid with the exclusion of Gly, and $R^4$ is H or the side chain of Thr, Ser, Asn, Asp, Glu, Gln, Lys, Arg or His, or when d is 1, e is 0, g is 0 or an integer from 1 to 3, h is an integer of 1 to 10, then $R^1$ is OH or $NH_2$, $R^2$ is H or $CH_3C(O)$, $R^3$ is $R'$—$(X)_q$ or $R'$—$(X)_q$—L, wherein R' is the side chain of Thr, Ser, Tyr, Cys, His, Asp, Glu, Lys or Trp, and $R^4$ is H or the side chain of Thr, Ser, Asn, Asp, Glu, Gln, Lys, Arg or His, or when d is 0 or an integer from 1 to 10, e is 0 or an integer from 1 to 3, g and h are 0, then $R^1$ is OH or $NH_2$, $R^2$ is $(X)_q$ or $(X)_q$—L, and $R^4$ is H or the side chain of a naturally occurring amino acid with the exclusion of Gly, or when d is 0 or an integer from 1 to 10, e is 0 or an integer from 1 to 3, g and h are 0, then $R^1$ is OH or $NH_2$, $R^2$ is H or $CH_3C(O)$, and $R^4$ is $R'$—$(X)_q$ or $R'$—$(X)_q$—L, wherein R' is the side chain of Thr, Ser, Tyr, Cys, His, Asp, Glu, Lys or Trp, and each L may be identical or different and designate a label, and q is 0 or an integer from 1 to 20.

6. The method according to claim 1, wherein f is an integer from 8 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, each X may be identical or different and selected from a group of hydrophilic linker units, d and h are 1, e is 0, g is 0 or an integer from 1 to 3, $R^1$ is $NH_2$, $R^2$ is H, $R^3$ is $R'$—$(X)_q$—L, where R' is the side chain of Lys, and $R^4$ is H or the side chain of Thr, Ser, Asn, Asp, Glu, Gln, Lys, Arg or His, and each L designates a label, and q is 0 or an integer from 1 to 20.

7. The method according to claim 1, wherein f is an integer from 8 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, each X may be identical or different and selected from a group of hydrophilic linker units, d is 1, e is 0, g is an integer from 1 to 3, h is an integer 1 to 10, $R^1$ is $NH_2$, $R^2$ is H, $R^3$ is H or the side chain of a naturally occurring amino acid with the exclusion of Gly, and $R^4$ is H or the side chain of Thr, Ser, Asn, Asp, Glu, Gln, Lys, Arg or His.

8. The method according to claim 1, wherein f is an integer from 8 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, each X may be identical or different and selected from a group of hydrophilic linker units, d, g and h are 0, e is 0 or an integer from 1 to 3, $R^1$ is $NH_2$, and $R^2$ is L or $CH_3C(O)$, and L designates a label.

9. The method according to claim 1, wherein the label L is biotin, 5-(and 6)-carboxyfluorescein, fluorescein isothiocyanate or dinitro benzoic acid.

10. The method according to claim 1, wherein f is an integer from 13 to 20, each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, d, e, g and h are 0, $R^1$ is $NH_2$, $R^2$ is $(X)_q$—L or $CH_3C(O)$, wherein each X is —$NH(CH_2CH_2O)_nCH_2C(O)$—, L is 5-(and 6)-carboxyfluorescein, fluorescein isothiocyanate, biotin or dinitro benzoic acid, n is an integer from 1 to 6, preferably from 1 to 3, and q is an integer from 1 to 3.

11. The method according to claim 1 characterized in that the probe is selected among probes of the general formula (Ia) which are probes of the general formula (I) wherein d, e, g and h are 0

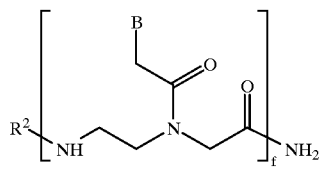

(Ia)

wherein each B is selected from the group consisting of the nucleobases thymine, adenine, cytosine, guanine and uracil, and non-naturally occurring nucleobases, in a sequence enabling the probe to hybridize to 16S or 23S rRNA or DNA sequences from the area coding for said rRNA of Neisseria gonorrhoeae or Chlamydia trachomatis, and f is 20; $R^2$ is $(X)_q$—L, wherein X is —$NH(CH_2CH_2O)_2CH_2C(O)$—; q is 1 or 2 and L is biotin;

f is 18; $R^2$ is $(X)_q$—L, wherein X is —$NH(CH_2CH_2O)_2CH_2C(O)$—; q is 1 or 2 and L is biotin;

f is 18; $R^2$ is $(X)_q$—L, wherein X is —$NH(CH_2CH_2O)_2CH_2C(O)$—; q is 1 or 2 and L is 5-(and 6)-carboxyfluorescein or fluorescein isothiocyanate;

f is 17; $R^2$ is $(X)_q$—L, wherein X is —$NH(CH_2CH_2O)_2CH_2C(O)$—; q is 1 or 2 and L is 5-(and 6)-carboxyfluorescein or fluorescein isothiocyanate;

f is 16; $R^2$ is $(X)_q$—L, wherein X is —$NH(CH_2CH_2O)_2CH_2C(O)$—; q is 1 or 2 and L is biotin;

f is 15; $R^2$ is $(X)_q$—L, wherein X is —$NH(CH_2CH_2O)_2CH_2C(O)$—; q is 1 or 2 and L is 5-(and 6)-carboxyfluorescein or fluorescein isothiocyanate;

f is 15; $R^2$ is $(X)_q$—L, wherein X is —$NH(CH_2CH_2O)_2CH_2C(O)$—; q is 1 or 2 and L is dinitro benzoic acid;

f is 15; $R^2$ is $(X)_3$, wherein $(X)_3$ is $HO(O)CCH_2C(O)(NH-(CH_2CH_2O)_2CH2C(O))_2$—; and f is 13; $R^2$ is $(X)_q$—L, wherein X is —$NH(CH_2CH_2O)_2CH_2C(O)$—; q is 1 or 2 and L is 5-(and 6)-carboxyfluorescein or fluorescein isothiocyanate.

12. The method according to claim 1 for detecting Neisseria gonorrhoeae, wherein each B is selected from the group consisting of the nucleobases thymine, adenine, cytosine, guanine and uracil, in a sequence comprising all or part of one of the Neisseria gonorrhoeae specific sequences 1a to 5a to allow hybridization to target sequences in 16S rRNA of Neisseria gonorrhoeae or to DNA sequences from the area coding for said rRNA.

13. The method according to claim 1 for detecting Neisseria gonorrhoeae, wherein each B is selected from the group consisting of the nucleobases thymine, adenine, cytosine, guanine and uracil, in a sequence comprising all or part of one of the Neisseria gonorrhoeae specific sequences 6a to 9a to allow hybridization to target sequences in 23S rRNA of Neisseria gonorrhoeae or to DNA sequences from the area coding for said rRNA.

14. The method according to claim 1 for detecting Chlamydia trachomatis, wherein each B is selected from the group consisting of the nucleobases thymine, adenine, cytosine, guanine and uracil, in a sequence comprising all or part of one of the Chlamydia trachomatis specific sequences 10a to 20a to allow hybridization to target sequences in 16S rRNA of Chlamydia trachomatis or to DNA sequences from the area coding for said rRNA.

15. The method according to claim 1 for detecting Chlamydia trachomatis, wherein each B is selected from the group consisting of the nucleobases thymine, adenine, cytosine, guanine and uracil, in a sequence comprising all or part of one of the Chiamydia trachomatis specific sequences 21a to 33a to allow hybridization to target sequences in 23S rRNA of Chlamydia trachomatis or to DNA sequences from the area coding for said rRNA.

16. A method according to claim 1, characterized in that the hybridization complex is captured on a solid phase before measuring the extent of hybridization.

17. A method according to claim 1, characterized in that a PNA probe according to claim 1 is used in capturing the hybridization complex.

18. A method according to claim 1, characterized in that in measuring the resulting hybridization a signal amplifying system is used.

19. Kit for detecting Neisseria gonorrhoeae and/or Chlamydia trachomatis, characterized in that it comprises at least one PNA probe and a detection system with at least one detecting reagent, wherein said PNA probe comprises from 6 to 30 N-(2-aminoethyl)glycine units in peptide linkage with the glycine nitrogen connected to naturally occurring nucleobases or non-naturally occurring nucleobases by a methylene carbonyl linker or connected to a labelling group and said probe capable of hybridizing to target sequences in 16S or 23S rRNA or DNA from the area coding for said rRNA of Neisseria gonorrhoeae or Chlamydia trachomatis.

20. Kit according to claim 19, characterized in that it furthermore comprises a solid phase capture system.

21. Kit according to claim 20, characterized in that the detection system comprises a signal amplifying system.

22. An assay for detecting rRNA which may be present in a test sample, comprising:

a. fixing said test sample and thereafter contacting said fixed test sample in situ with a peptide nucleic acid (PNA) probe capable of attaching to said rRNA in said test sample conjugated to an indicator reagent comprising signal generating compound capable of generating a measurable signal; and b. detecting said measurable signal as an indication of the presence of rRNA in the test sample.

23. The assay of claim 22, wherein quantitation is performed by exciting fluorescence.

24. The assay of claim 22, wherein said signal generating compound is fluorescein.

25. In a fluorescence in situ hybridization assay for detecting the presence of rRNA which may be present in a test sample comprising the steps of (a) fixing said test sample, (b) hybridizing said rRNA in said test sample with a probe capable of attaching to said rRNA in said test sample conjugated to a signal generating compound capable of generating a measurable signal and (c) detecting the presence of rRNA in said test sample by measuring the detectable signal, wherein the improvement comprises hybridizing said test sample with a peptide nucleic acid (PNA) probe.

26. The fluorescence in situ hybridization assay of claim 25, wherein said signal generating compound is fluorescein.

27. A method for detecting rRNA in a sample, comprising the steps of:

(a) contacting a smear of bacterial cells with one or more PNA probes, under conditions suitable for in situ hybridization to occur between the PNA probes(s) and any target rRNA in the sample; and (b) detecting any complexes formed between said PNA probes(s) and said bacterial rRNA.

28. The method of claim 27 wherein the assay format is fluorescence in situ hybridization.

29. The method of claim 28, wherein said PNA probe(s) are labeled with fluorescein.

30. A method for detecting an rRNA or rDNA target, comprising the steps of:

(a) releasing nucleic acid from bacteria present in a test sample;

(b) contacting one or more detectably labeled PNA probes with rRNA or rDNA target in solution under conditions which promote hybridization between the PNA probe and any target nucleic acid present and (c) detecting the PNA-nucleic acid complex formed.

31. The method of claim 30, wherein the PNA-nucleic acid complex is immobilized to a solid support.

32. The method of claim 31, wherein the PNA-nucleic acid complex is immobilized to a solid support using a capture probe.

33. The method of claim 31, wherein the PNA-nucleic acid complex is immobilized to a solid support using a capture antibody specific for PNA-nucleic acid complexes.

34. The method of claim 31, wherein said PNA probes(s) are immobilized to a solid support.

35. The method of claim 32 wherein, the capture probe is a species specific PNA probe not used in the hybridization reaction for detecting the target nucleic acid.

36. The method of claim 30, wherein said PNA-nucleic acid complex is detected using a primary antibody which reacts specifically with PNA-nucleic acid complexes.

37. The method of claim 36, wherein said primary antibody comprises a label.

38. The method of claim 36, wherein said primary antibody is unlabeled, and the detection system comprises a labeled secondary antibody which specifically binds to said primary antibody.

* * * * *